US008053400B2

(12) United States Patent
Dong et al.

(10) Patent No.: US 8,053,400 B2
(45) Date of Patent: Nov. 8, 2011

(54) LIQUID CLEANSING COMPOSITION COMPRISING A TERNARY MIXTURE OF ANIONIC SURFACTANTS

(75) Inventors: Xue Min Dong, Lincolnhshire, IL (US); Branko Sajic, Lincolnwood, IL (US); Irene Shapiro, Buffalo Grove, IL (US); Minh Tong, Lindenhurst, IL (US); John Frank Zamorski, Cranford, NJ (US)

(73) Assignee: Stepan Company, Northfield, IL (US)

( * ) Notice: Subject to any disclaimer, the term of this patent is extended or adjusted under 35 U.S.C. 154(b) by 576 days.

(21) Appl. No.: 11/814,043

(22) PCT Filed: Feb. 3, 2006

(86) PCT No.: PCT/US2006/003962
§ 371 (c)(1),
(2), (4) Date: Feb. 11, 2009

(87) PCT Pub. No.: WO2006/084190
PCT Pub. Date: Aug. 10, 2006

(65) Prior Publication Data
US 2009/0227482 A1    Sep. 10, 2009

Related U.S. Application Data

(60) Provisional application No. 60/650,020, filed on Feb. 4, 2005.

(51) Int. Cl.
*C11D 1/37* (2006.01)
(52) U.S. Cl. ........ 510/125; 510/119; 510/127; 510/130; 510/155; 510/156; 510/357; 510/414; 510/426; 510/427; 510/248
(58) Field of Classification Search .......... 510/119, 510/125, 127, 130, 155, 156, 357, 414, 426, 510/427, 428
See application file for complete search history.

(56) References Cited

U.S. PATENT DOCUMENTS

| | | | | |
|---|---|---|---|---|
| 5,637,758 A | * | 6/1997 | Sajic et al. | 560/147 |
| 5,891,839 A | * | 4/1999 | Erilli et al. | 510/426 |
| 6,139,828 A | * | 10/2000 | McCullough | 424/70.24 |
| 6,225,485 B1 | * | 5/2001 | Bertz et al. | 554/148 |
| 6,723,688 B1 | * | 4/2004 | Malik et al. | 510/130 |
| 2004/0071653 A1 | * | 4/2004 | Bratescu et al. | 424/70.24 |
| 2004/0110650 A1 | * | 6/2004 | Siddiqui et al. | 510/119 |
| 2004/0234484 A1 | * | 11/2004 | Peffly et al. | 424/70.13 |
| 2004/0259744 A1 | * | 12/2004 | Yang et al. | 510/127 |
| 2006/0110415 A1 | * | 5/2006 | Gupta | 424/401 |
| 2006/0135383 A1 | * | 6/2006 | Cossa et al. | 510/130 |
| 2006/0257439 A1 | * | 11/2006 | Sabnis et al. | 424/401 |
| 2007/0004611 A1 | * | 1/2007 | Ospinal et al. | 510/152 |
| 2008/0058236 A1 | * | 3/2008 | Ospinal et al. | 510/141 |
| 2009/0074691 A1 | * | 3/2009 | Gupta | 424/62 |
| 2009/0074888 A1 | * | 3/2009 | Bhatia et al. | 424/705 |
| 2009/0252815 A1 | * | 10/2009 | Walzer et al. | 424/616 |

OTHER PUBLICATIONS

European Search Report corresponding to European Application Serial No. 06720279.6.

* cited by examiner

*Primary Examiner* — Charles Boyer
(74) *Attorney, Agent, or Firm* — McAndrews, Held & Malloy, Ltd.

(57) ABSTRACT

A personal cleansing composition exhibiting enhanced skin feel (i.e., enhanced skin softness, reduced skin irritation, reduced residue, and reduced greasy, tacky, or tight skin feel), enhanced foaming and lather, and good cleansing, more specifically, a personal cleansing composition comprising a mixture of alpha sulfonated alkyl esters or sulfonated fatty acids, or salts thereof, with an alkyl sulfoacetate or ethoxylated alkyl sulfoacetate, or salts thereof, secondary surfactants, and optional additives.

23 Claims, 1 Drawing Sheet

LIQUID CLEANSING COMPOSITION COMPRISING A TERNARY MIXTURE OF ANIONIC SURFACTANTS

CROSS-REFERENCE TO RELATED APPLICATIONS/INCORPORATION BY REFERENCE

This application makes reference to, claims priority to, and claims the benefit of U.S. Provisional Application Ser. No. 60/650,020 filed on Feb. 4, 2005.

FIELD OF THE INVENTION

The invention generally relates to a personal skin or hair cleansing composition, more specifically, an aqueous personal cleansing composition comprising a mixture of alpha sulfonated alkyl esters or sulfonated fatty acids with an alkyl sulfoacetate or ethoxylated alkyl sulfoacetate.

BACKGROUND OF THE INVENTION

The development of personal cleansers (including, without limitation, liquid hand soaps, body washes, shampoos, bath washes, and the like) has long been driven by the challenge of providing a combination of performance properties such as good foaming, good cleansing, enhanced mildness, improved skin feel, and attractive product appearance. Specifically, while a certain component within a personal cleanser may enhance one property, it will often do so at the detriment of another important property of the cleansing product. For example, a composition may enhance skin conditioning by incorporating emollients at the expense of foaming. Therefore, those in the relevant art have been seeking new formulations to help achieve the balance of desirable performance properties.

It is well known that a personal cleanser is typically aqueous and comprises one or more mild detersive surfactants and/or soaps. For example, conventional hand cleansers, body washes, shampoos, or liquid soap typically comprise a synthetic detersive and/or fatty acid soap and one or more foam stabilizing, wetting, or emulsifying surfactants.

Similarly, personal cleansers based on synthetic detergents often impart poor skin feel during and after use, and require additives to improve such tactile aspects of performance. Further, synthetic detergents often degrease the skin to an excessive degree thereby resulting in dry skin.

Therefore, researchers have strived to develop a personal cleansing formulation with low irritation, good tactile characteristics, good foaming, and good cleansing properties. Examples of developments in synthetic personal cleansing formulations include U.S. Pat. No. 4,664,835, which describes a washing and cleansing formulation containing a synthetic surfactant and an anionic polymer; U.S. Pat. No. 5,646,100, which describes a liquid personal cleansing formulation containing an anionic surfactant, a betaine, and an alkyl polyglycoside; and U.S. Pat. No. 5,310,508, which describes a personal cleansing composition containing a salt of alcohol ethoxy glyceryl sulfonate ("AGS") and a second synthetic surfactant.

Examples of liquid cleansers which provide both cleansing and moisturizing functions include U.S. Pat. No. 5,650,384, which describes cleansing and moisturizing emulsions containing two phases. One of the phases is a moisturizing phase comprising 0.5% to about 33.5% of a skin conditioning ingredient, which may be a vegetable oil, petrolatum or silicone oil, among others. Another patent, U.S. Pat. No. 5,965,500, describes liquid cleansing compositions containing levels of oil/emollient equal to or greater than the level of surfactant. The surfactant system contains at least one anionic surfactant, which may be an aliphatic or aromatic sulfonate. U.S. Pat. No. 5,661,189 describes liquid cleansing compositions which contain from 0.1 to 15% of a "benefit agent" which may be, for example, vegetable, mineral or silicone oils.

These developments, and other conventional personal cleansers, however, fail to provide the desired balance of skin feel (i.e., skin softness, smoothness, moisturization, no greasy and low skin irritation), foaming, lather, and cleansing. Accordingly, there remains a need for a personal cleansing formulation that provides enhanced skin feel, low skin irritation, low skin drying, good cleansing ability, good foaming, and good rinsability characteristics/properties.

SUMMARY OF THE INVENTION

The presently described technology embodying a personal cleanser and method of making the same provides one or more of the following advantages over conventional personal cleansers, including, without limitation, enhanced skin feel, low skin drying, high lather and foaming, good cleansing, low skin irritation and, when used as a shampoo, hair color fastness. Other objects of the presently disclosed technology will become apparent to those skilled in the art who have the benefit of this specification and the conventional art.

In one embodiment, there is provided a personal cleansing composition comprising between about 0.1% to about 70% by weight of a primary surfactant mixture, between about 0.1% to about 50% by weight of secondary surfactants, and between about 20% to about 99% water. The primary surfactant mixture is preferably comprised of a mixture of (i) an alpha sulfonated alkyl ester, a sulfonated fatty acid, salts thereof, or a mixture thereof; and (ii) an alkyl sulfoacetate, an ethoxylated alkyl sulfoacetate, salts thereof, or a mixture thereof, in a ratio of (I) to (ii) of preferably between about 1:1.5 to about 10:1.

In another embodiment of the present technology there is provided a process for producing a primary surfactant mixture comprising (i) mixing an alkyl or ethoxylated alkyl alcohol mono-chloroacetate with an α-sulfo alkyl ester and/or an α-sulfo alkyl fatty acid, (ii) sulfitating the mixture with sodium sulfite and sodium metabisulfite to produce a mixture of alkyl sulfoacetate and/or ethoxylated alkyl sulfoacetate and alpha sulfonated alkyl ester and/or alpha sulfonated fatty acid, in a ratio of sulfonated alkyl ester/sulfonated fatty acid to alkyl sulfoacetate/ethoxylated alkyl sulfoacetate of between about 1:1.5 to about 10:1; and (iii) neutralizing the mixture with an alkaline solution to produce a primary surfactant mixture comprising between about 0.5% to about 70% by weight total surfactant.

In a further embodiment, there is provided a composition suitable for use as a liquid hand soap, liquid body wash, or shampoo, including: 1) a primary surfactant mixture in an amount between about 0.1% to about 70% of the total cleansing composition; 2) between about 0.1% to about 50% by weight of secondary surfactants; 3) between about 0.1% to about 50% by weight of additives; 4) water. The primary surfactant mixture preferably comprises a mixture of (i) a sulfonated alkyl ester, or salts thereof, and/or a sulfonated fatty acid, or salts thereof, and (ii) an alkyl sulfoacetate, or salts thereof, and/or an ethoxylated alkyl sulfoacetate, or salts thereof, in a ratio of (i) to (ii) of between about 1:1.5 to about 10:1. It will be understood that while specific ingredients may be utilized in any amount within the specified ranges, that the relative amounts of ingredients and/or optional additives or thickeners selected shall add to 100% of a finished composition.

In a further embodiment, there is provided a colorfast shampoo composition including: 1) a primary surfactant mixture in an amount of from about 5 to about 25 weight percent active; 2) from about 0.5 to about 10 weight percent active of a secondary surfactant; 3) from about 0.1 to about 10 weight percent of additives; and 4) water. The primary surfactant mixture comprises a mixture of (i) a sulfonated alkyl ester, or salts thereof, and/or a sulfonated fatty acid, or salts thereof, and (ii) an alkyl sulfoacetate, or salts thereof, and/or an ethoxylated alkyl sulfoacetate, or salts thereof, in a ratio of (i) to (ii) of about 10:1 to about 1:10.

Further embodiments of the present invention may additionally incorporate emollients, skin conditioners, viscosity adjusters, rheological modifiers, fragrances, colorants, opacifiers, pearlescent agents, herbal extract, vitamins and the like. Additional embodiments may also be configured to be suitable as soap powder, shower gel, bath soap or bath beads, dishwashing detergent, or denture cleanser.

While the presently described technology will be described in connection with one or more preferred embodiments, it will be understood by those skilled in the art that it is not limited to those embodiments. On the contrary, the presently described technology includes all alternatives, modifications, and equivalents as may be included within the spirit and scope of the appended claims.

DETAILED DESCRIPTION OF THE INVENTION

Figure 1:
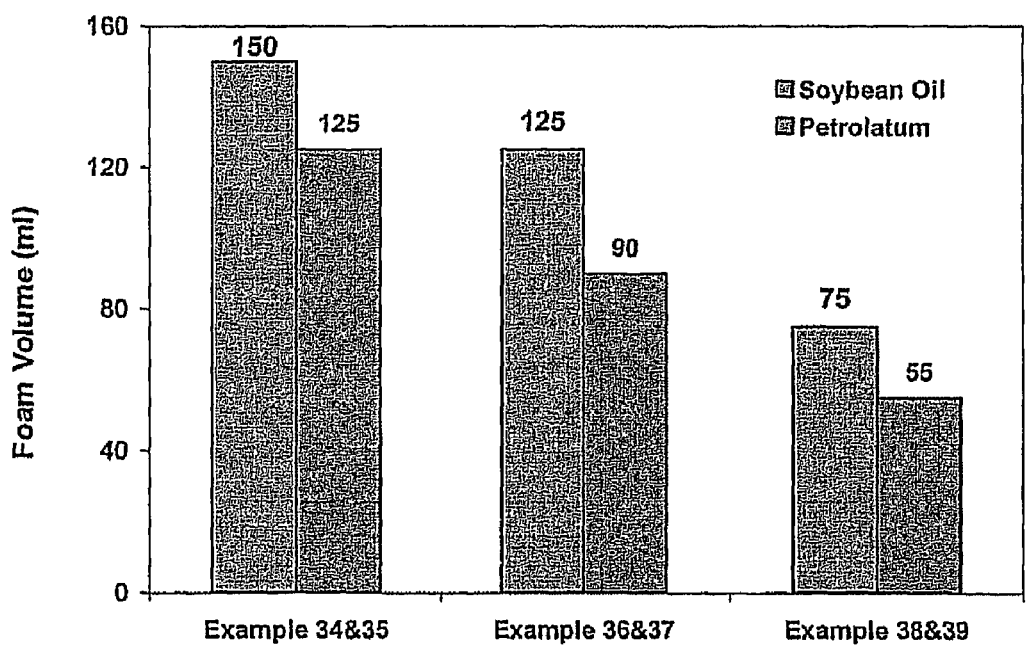
FIG. 1 is a graph comparing the foaming performance of personal cleansing compositions prepared in accordance with the present technology with control compositions.

The personal cleansing compositions of the present invention preferably exhibit enhanced skin feel, low skin irritation, low skin drying, good cleansing ability, good foaming, and good rinsability characteristics/properties. Preferably, the present personal cleansing compositions also do not leave the skin feeling tacky or tight during drying. The cleansing compositions may be utilized alone, as skin or body washes, or may be utilized with soaps, thickeners, additives, or the like to produce various liquid soap-based or synthetic hand cleansers, face cleansers, body washes, bath soaps, bath beads, shower gels, shampoos, dish washing liquids, denture cleansers, and the like.

In one embodiment, there is provided a personal cleansing composition comprising between about 0.1% to about 70% by weight of a primary surfactant mixture, between about 0.1% to about 50% by weight of a secondary surfactant, between about 20% to about 99% water, and between about 0% to about 70% optional ingredients. The primary surfactant mixture is preferably comprised of a mixture of (i) an alpha sulfonated alkyl ester, a sulfonated fatty acid, or a mixture thereof; and (ii) an alkyl sulfoacetate, an ethoxylated alkyl sulfoacetate, or a mixture thereof, in a ratio of (i) to (ii) of between about 1:1.5 to about 10:1. It will be understood that while specific ingredients may be utilized in any amount within the specified ranges, that the relative amounts of ingredients and/or optional additives or thickeners selected shall add to 100% of a finished composition.

Primary Surfactant Mixture:

The primary surfactant mixture of the presently described technology is preferably comprised of a mixture of (i) an alpha sulfonated alkyl ester, a sulfonated fatty acid, or a mixture thereof (hereinafter "SME/SFA"), and (ii) an alkyl sulfoacetate, an ethoxylated alkyl sulfoacetate, or a mixture thereof (hereinafter "ASA/EASA"). It should be understood that the terms "alpha sulfonated alkyl ester" and "sulfonated fatty acid" as used herein include the salts thereof. It should also be understood that the terms "alkyl sulfoacetate" and "ethoxylated alkyl sulfoacetate" as used herein include the salts thereof. Preferably, the primary surfactant mixture comprises a majority of SME/SFA. Stated differently, the primary surfactant mixture is preferably comprised of a ratio of SME/SFA to ASA/EASA of between about 1:1.5 to about 10:1, more preferably between about 1:1 to about 5:1, and most preferably, between about 1:1 to about 3:1.

While not intending to be limited to any one theory, it is believed that a primary surfactant mixture comprised of both SME/SFA and ASA/EASA exhibits unexpected high foaming and pleasant skin feel properties over a cleansing composition comprising either surfactant mixture alone. Furthermore, it is believed that a cleansing composition comprising a primary surfactant mixture of SME/SFA and ASA/EASA, exhibits, among other desirable properties, good cleansing and mildness properties. The incorporation of the surfactant mixture of the presently described technology may also lower the total cost of a final cleansing composition.

Preferably, the primary surfactant mixture comprises between about 0.1% to about 70% of the total weight of a finished personal cleansing composition. More preferably, liquid personal cleansers of the present invention utilize between about 5% to about 35% primary surfactant mixture by weight of the total finished cleansing composition, and most preferably, between about 10% to about 15% by weight. For a colorfast shampoo composition, the primary surfactant mixture preferably is present in an amount of about 5 to about 25 weight percent active.

Alpha Sulfonated Alkyl Ester/Sulfonated Fatty Acid ("SME/SFA")

Preferably, one component of the primary surfactant mixture of the presently described technology is an alpha sulfonated alkyl ester, an alpha sulfonated fatty acid, or a mixture thereof. The alpha sulfonated alkyl ester preferably has the following general formula:

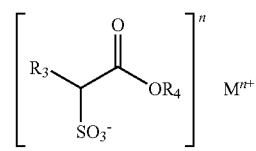

wherein $R_3$ is a fully saturated or unsaturated $C_6$-$C_{22}$ hydrocarbyl group, an alkyl group, or combination thereof, $R_4$ is a straight or branched chain $C_1$-$C_6$ hydrocarbyl group, an alkyl group, or combination thereof, n is 1 or 2 and M is hydrogen, sodium, potassium, calcium, magnesium, ammonium, monoethanolammonium, diethanolammonium, triethanolammonium, or a mixture thereof.

The sulfonated fatty acid preferably has the general formula:

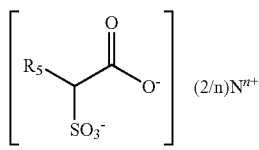

wherein $R_5$ is a fully saturated or unsaturated $C_6$-$C_{22}$ hydrocarbyl group, an alkyl group, or combination thereof, n is 1 or 2 and wherein N is hydrogen, sodium, potassium, calcium, magnesium, ammonium, monoethanolammonium, diethanolammonium, triethanolammonium, or a mixture thereof.

Embodiments of the present technology may contain SME or SFA alone, or a mixture of the two. Some embodiments which utilize mixtures of SME and SFA preferably utilize a ratio of such components of from about 30:1 to about 0:1, more preferably a ratio of from about 10:1 to about 1:10, and most preferably, a ratio of from about 7:1 to about 1:1. When alkyl esters are sulfonated, as discussed below, the alpha sulfonated alkyl esters normally contain a minor amount, typically not exceeding 33% by weight of the total sulfonated product, of a sulfonated fatty acid (i.e., di-salt), which results from hydrolysis of the ester. Generally, larger amounts of the di-salt are obtained by hydrolyzing a known amount of the mono-salt; hydrolysis may be accomplished in situ during the preparation of the composition. Accordingly, the alpha sulfonated alkyl ester and alpha sulfonated fatty acid may be utilized in the composition or process of the presently described technology as a blend of components which naturally result from the sulfitation of an alkyl ester of a fatty acid, or as individual components. Furthermore, it is known to one skilled in the art that minor impurities, including by way of example, sodium sulfate, unsulfonated methyl esters (ME), and unsulfonated fatty acids (FA) may also be present in the mixtures according to the present technology.

The alpha sulfonated alkyl esters, i.e., alkyl ester sulfonate surfactants, can include, for example, linear esters of $C_6$-$C_{22}$ carboxylic acid (i.e., fatty acids) which are sulfonated with gaseous $SO_3$ according to the "The Journal of American Oil Chemists Society," Vol. 52 at 323-329 (1975). Suitable starting materials include, among others, natural fatty substances as derived from tallow, palm oil, etc. In some preferred embodiments of the presently described technology, the α-sulfonated alkyl ester is a sulfonated methyl ester.

Some suitable commercially available mixtures of SME and SFA may be obtained from Stepan Company, Northfield, Ill., such as ALPHA-STEP® BSS-45, ALPHA-STEP® MC-48 or ALPHA-STEP® PC-48 (sodium methyl 2-sulfolaurate and disodium 2-sulfolaurate).

Alkyl Sulfoacetate/Ethoxylated Alkyl Sulfoacetate ("ASA/EASA")

The alkyl sulfoacetate or ethoxylated alkyl sulfoacetate preferably has the general chemical structure:

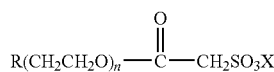

Wherein R is a fully saturated or unsaturated $C_5$-$C_{21}$ hydrocarbyl group, n is an integer between 0 and 6, and X is hydrogen, an alkaline metal, ammonium, organic amine, or alkaline earth metal. Preferred ASA or EASA include, without limitation, sodium lauryl sulfoacetate, ethoxylated sodium lauryl sulfoacetate.

It should be understood by those skilled in the art that suitable ASA or EASA for purposes of the presently described technology may be produced by sulfitating an alkyl alcohol mono-chloroacetate with a sulfitating agent such as sodium sulfite and sodium metabisulfite, or may be commercially obtained from Stepan Company, Northfield Ill., as LATHANOL® LAL (sodium lauryl sulfoacetate).

The primary surfactant mixture described in the present technology can be prepared by physically blending SME/SFA with ASA or EASA at a desired active ratio. Alternatively, in some embodiments of the presently described technology, the primary surfactant mixture may be prepared by sulfitating an alkyl or ethoxylated alkyl alcohol mono-chloroacetate in the presence of an alpha sulfo alkyl ester and/or of an alpha sulfo fatty acid with a sulfitating agent such as sodium sulfite and sodium metabisulfite, followed by co-neutralization with a base, such as sodium hydroxide, potassium hydroxide, calcium hydroxide, magnesium oxide, monoethanolamine, diethanolamine or triethanolamine, or a mixture thereof. It has been found that sulfitation of alkyl alcohol mono-chloroacetate in presence of an alpha sulfo alkyl ester and/or of an alpha sulfo fatty acid will efficiently reduce the viscosity of the mixture during processing to produce a surfactant mixture of alpha sulfonated alkyl ester, sulfonated fatty acid, alkyl sulfoacetate and/or ethoxylated alkyl sulfoacetate. In-situ sulfitation alleviates the need for separately producing and mixing the components of the primary surfactant mixture.

Secondary Surfactant:

Preferred embodiments of the presently described invention may also include a secondary surfactant, which is believed may act as an additional detersive, foam stabilizer, wetting agent, emulsifier, skin enhancer, viscosity modifier or the like.

The secondary surfactant may be a suitable anionic, nonionic, cationic, amphoteric, or zwitterionic surfactant, and preferably comprises between about 0.1% to about 50% by weight of the total cleansing composition, more preferably, between about 1% to about 15% by weight of the total cleansing composition, and most preferably, between about 2% to about 10% by weight of the total cleansing composition. For a colorfast shampoo composition, the secondary surfactant may be present in an amount of about 0.5 to about 10 weight percent active.

Suitable anionic surfactants, include, without limitation: sulfonated alkyl benzene, sulfonated alpha olefin, paraffin sulfonate, alkyl sulfate, alkyl alkoxy sulfate, alkyl alkoxy carboxylate, alkyl phosphate, alkyl alkoxy phosphate, alkyl sulfonate, alkyl alkoxylated sulfate, acyl lactylate, alkyl isethionate, salts thereof, and combinations thereof. Further examples can be found in "Surface Active Agents and Detergents" (Vol. I and II by Schwartz, Perry and Berch). Suitable nonionic surfactants include, without limitation: fatty acid amide, ethoxylated fatty acid amide, alkyl alcohol, alkyl alcohol ethoxylate, alkyl phenol ethoxylate, propylene glycol esters, polyglycerol esters, ethylene glycol esters, ethoxylated glycol esters, polypropylene glycol esters, alkylpolyglycoside, alkyl glucamide, and combinations thereof. More examples are generally disclosed in U.S. Pat. No. 3,929,678 to Laughlin et al., issued on Dec. 30, 1975 at column 13, line 14 through column 16, line 6, incorporated herein by reference. Cationic surfactants and cationic polymers may include, without limitation: alkyl dimethylammonium halogenide, quaternized cellulose, quaternized quar gum, esterquat, amidoquat, and stearylammidopropyl dimethyl amine quat. Other cationic surfactants useful herein are also described in U.S. Pat. No. 4,228,044 to Cambre, issued Oct. 14, 1980, incorporated herein by reference. Other suitable secondary surfactants include, for example, betaines, amine oxide, fatty acid amide, ethoxylated fatty acid amide and acyl lactylate.

Most preferably, the secondary surfactant is an anionic surfactant, betaine, amine oxide, fatty acid amide, ethoxylated fatty acid amide, hydroxysultaine, sulfosuccinate, amphoacetate, sarcosinate, or acyl lactylate. Suitable commercially available secondary surfactants include, without limitation, the AMPHOSOL® series (betaines and sultaines), AMMONYX® LMDO (lauramidopropylamine/myristamidopropylamine oxide), or AMMONYX® LO-E (lauramine oxide), NINOL® C-5 and NINOL® COMF surfactants manufactured by Stepan Company, Northfield, Ill., or other surfactants disclosed and discussed below in the Examples.

Water:

The cleanser compositions described herein are preferably in the form of liquids or creams in which water is the principal diluent. Alternatively, although less preferred, other solvents such as alcohols may be utilized. The level of water in a liquid personal cleansing composition is preferably from about 30% to about 99% by weight, more preferably from about 70% to about 90% by weight, and most preferably between about 80% to about 90% by weight.

Optional Ingredients:

The formulations of the presently described technology may be used alone as a liquid cleansing composition, preferably as a body wash, hand wash, shampoo or the like. Alternatively, other optional ingredients may be added to make the present compositions more preferable for a variety of different uses such as a pumpable liquid hand cleanser, denture cleanser, dish soap, gel body wash, face cleanser, bath soap, or the like.

For example, while not bound to any one theory, it is believed that fatty acid soaps, polymeric thickeners, humectants, electrolytes, rheological modifiers, fatty alcohols, fatty glycerol, opacifiers, pearlescent agents and PEG esters may be added to achieve a desired viscosity and phase stability for the finished cleansing composition. If the cleansing composition is to be formulated as a dish soap or pumpable hand cleanser, it is desirable that the composition have a viscosity which is pleasing to the feel, but allows a proper quantity of the formulation to be readily delivered through an appropriately sized aperture of a hand pumped delivery apparatus.

Alternatively, the liquid cleansing products can be thickened by using polymeric additives that hydrate, swell or molecularly associate to provide body (e.g., hydroxypropyl guar gum is used as a thickening aid in shampoo compositions). Suitable thickening agents include, without limitation, those listed in the Glossary and Chapters 3, 4, 12 and 13 of the *Handbook of Water-Soluble Gums and Resins*, Robert L. Davidson, McGraw-Hill Book Co., New York, N.Y., 1980. Preferably, cellulosic polymers and acrylic polymers and copolymers may be utilized, preferably in an amount between about 0.1% to about 10% by weight of the finished cleansing composition, more preferably, between about 0.3% to about 5% by weight. Other suitable rheological modifiers include, without limitation, polyacrylic acid, polyacrylate, polyvinyl alcohol, polyethylene glycol, polyethylene glycol ester, and inorganic salts, including, without limitation, potassium chloride, magnesium chloride, sodium chloride, calcium chloride, sodium sulfate, potassium sulfate, and magnesium sultate.

Emollients (including, without limitation, vegetable oils, mineral oils, silicone oils, petrolatum, polyglycerol methyl esters, and esters), skin conditioning agents (such as glycerine and free fatty acid), fragrances, herbal extracts, and vitamins may be added to further enhance skin conditioning ability. In some product formulations, such as body wash emulsions, it may be desirable to add emollients in amounts as high as 25% by weight or more of the total cleansing composition in order to enhance the skin moisturizing properties of the composition. Ordinarily, emollients are not added in such high amounts because they detrimentally affect the foaming properties of the cleansing composition. Surprisingly, however, the cleansing compositions of the present technology work almost synergistically with such emollients to provide unexpectedly good foaming performance. Stated another way, the emollients do not act as defoamers in the cleansing composition of the present technology. Without wishing to be bound by a particular theory, it is believed that the cleansing composition provides a high level of emulsification, generating a stronger oil-surfactant film which preserves the foam.

Fatty acid soaps, builders, and additional surfactants may be added to aid in cleansing ability. Fragrances and colors may also be added to further enhance the appearance and smell of the finished formulation. Suitable preservatives such as benzyl alcohol, methyl paraben, propyl paraben and imidazolidinyl urea may be utilized. Antibacterial agents such as quaternary ammonium compounds may also be utilized. Furthermore, a dimethyl polysiloxane may be utilized to enhance skin feel and conditioning properties to hair.

The compositions and the methods of producing such compositions herein may be formulated and carried out such that they will have a pH of between about 4.0 to about 8.5, and, in some embodiments, between about 5.0 to about 7.0. Techniques for controlling pH at recommended usage levels include the use of buffers, alkali, acids, etc., and are well known to those skilled in the art. Optional pH adjusting agents can include, but are not limited to citric acid, succinic acid, phosphoric acid, sodium hydroxide, sodium carbonate, and the like.

EXAMPLES

The following examples describe some of the preferred embodiments of the present technology without limiting the technology thereto. Other embodiments include, but are not limited to, those described in the above written description, including additional or alternative components, alternative concentrations, and additional or alternative properties and uses.

TABLE A

| Composition Trade Names & Abbreviations | |
|---|---|
| SME | alpha sulfonated alkyl ester |
| SFA | sulfonated fatty acid |
| ASA | alkyl sulfoacetate |
| EASA | ethoxylated alkyl sulfoacetate |

TABLE A-continued

| Composition Trade Names & Abbreviations | |
|---|---|
| ALPHA-STEP ® BSS-45 | average 1.6:1 ratio of sodium sulfonated methyl $C_{12}$-$C_{18}$ ester (and) disodium sulfonated $C_{12}$-$C_{18}$ fatty acid |
| ALPHA-STEP ® MC-48 | average 6:1 ratio of sodium sulfonated methyl $C_{12}$-$C_{18}$ ester (and) disodium sulfonated $C_{12}$-$C_{18}$ fatty acid |
| ALPHA-STEP ® PC-48 | average 6:1 ratio of sodium sulfonated methyl $C_{12}$-$C_{18}$ ester (and) disodium sulfonated $C_{12}$-$C_{18}$ fatty acid |
| ALPHA-STEP ® DS-85 | sodium salt of palm stearin sulfonated fatty acid |
| ALPHA-STEP ® PS-70 | sodium salt of palm stearin sulfonated methyl ester and sulfonated fatty acid (1:1 ratio) |
| ALPHA-STEP ® PS-65 | sodium salt of palm stearin sulfonated methyl ester and sulfonated fatty acid (10:1 ratio) |
| LATHANOL ® LAL | sodium lauryl sulfoacetate |
| STEOL ® CS-230 | sodium salt of $C_{12}$-$C_{14}$ alkyl ethoxy sulfate with 2 moles ethylene oxide per mole of alcohol |
| AMPHOSOL ® HCG | cocamidopropyl betaine |
| AMPHOSOL ® CS-50 | cocamidopropyl hydroxysultaine |
| AMPHOSOL ® CSF | sodium cocoamphopropionate |
| AMPHOSOL ® 1C | sodium cocoamphoacetate |
| PHOSP. NINOL C-4 | sodium salt of phosphated cocamide ethoxy (4 moles ethylene oxide) monoeththanol amine |
| SULFATED NINOL C-4 | sodium salt of sulfonated cocamide ethoxy (4 moles ethylene oxide) monoethanol amine |
| AMMONYX ® LMDO | lauric/myristicamidopropyl amine oxide |
| AMPHOSOL ® CB | cetyl betaine |
| NINOL CMP | cocamide monoethanol amine (MEA) |
| ZELEC ® UN | $C_8$-$C_{16}$ mono and di alkyl acid phosphate |
| ZELEC ® LA-2 | $C_{12}$-$C_{16}$ mono and di alkyl ethoxy acid phosphate |
| PGME | propylene glycol mono ester of vegetable/animal oil |
| COCO SUCCINAMATE | sodium salt of coco succinamate |
| $C_{12}$ SUCCINAMATE | sodium salt of $C_{12}$ succinamate |
| $C_{12}$ ACYL LACTYLATE | sodium salt of $C_{12}$ acyl lactylate |
| $C_{20}$-$C_{24}$ AOS | sodium salt of $C_{20}$-$C_{24}$ alpha olefin sulfonate |

Examples 1-23 are formulations of the presently described cleansing composition, without any additives or thickeners, indicated in weight percent active.

TABLE B

Examples 1-6 (formulations without additives)

| Ingredient | Example 1 Wt. % Active | 2 Wt. % Active | 3 Wt. % Active | 4 Wt. % Active | 5 Wt. % Active | 6 Wt. % Active |
|---|---|---|---|---|---|---|
| ALPHA-STEP ® PC-48 | 6.0 | 6.0 | 6.0 | 6.0 | 6.0 | 6.0 |
| LATHANOL ® LAL | 6.0 | 6.0 | 6.0 | 6.0 | 6.0 | 6.0 |
| AMPHOSOL ® CS-50 | 3.0 | | | | | |
| AMPHOSOL ® CSF | | 3.0 | | | | |
| AMPHOSOL ® CB | | | 3.0 | | | |
| PHOSP. NINOL C-4 | | | | 3.0 | | |
| SULFATED NINOL C-4 | | | | | 3.0 | |
| ALPHA-STEP ® DS-85 | | | | | | 3.0 |
| WATER | 85.0 | 85.0 | 85.0 | 85.0 | 85.0 | 85.0 |

TABLE C

Examples 7-12 (formulations without additives)

| Ingredient | Example 7 Wt. % Active | 8 Wt. % Active | 9 Wt. % Active | 10 Wt. % Active | 11 Wt. % Active | 12 Wt. % Active |
|---|---|---|---|---|---|---|
| ALPHA-STEP ® PC-48 | 6.0 | 6.0 | 6.0 | 6.0 | 6.0 | 6.0 |
| LATHANOL ® LAL | 6.0 | 6.0 | 6.0 | 6.0 | 6.0 | 6.0 |
| AMMONYX ® LMDO | 3.0 | | | | | |
| AMPHOSOL ® CB | | 3.0 | | | | |

TABLE C-continued

Examples 7-12 (formulations without additives)

| Ingredient | 7 Wt. % Active | 8 Wt. % Active | 9 Wt. % Active | 10 Wt. % Active | 11 Wt. % Active | 12 Wt. % Active |
|---|---|---|---|---|---|---|
| NINOL ® CMP | | | 3.0 | | | |
| ZELEC ® UN | | | | 3.0 | | |
| ZELEC ® LA-2 | | | | | 3.0 | |
| WATER | 85.0 | 85.0 | 85.0 | 85.0 | 85.0 | 85.0 |

TABLE D

Examples 13-18 (formulations without additives)

| Ingredient | 13 Wt. % Active | 14 Wt. % Active | 15 Wt. % Active | 16 Wt. % Active | 17 Wt. % Active | 18 Wt. % Active |
|---|---|---|---|---|---|---|
| ALPHA-STEP ® PC-48 | 6.0 | 6.0 | 6.0 | 6.0 | 6.0 | 6.0 |
| LATHANOL ® LAL | 6.0 | 6.0 | 6.0 | 6.0 | 6.0 | 6.0 |
| AMPHOSOL ® 1C | | | | | | 3.0 |
| PGME | 3.0 | | | | | |
| COCO SUCCINAMATE | | 3.0 | | | | |
| C12 SUCCINAMATE | | | 3.0 | | | |
| ACYL LACTYLATE | | | | 3.0 | | |
| C20-24 AOS | | | | | 3.0 | |
| WATER | 85.0 | 85.0 | 85.0 | 85.0 | 85.0 | 85.0 |

TABLE E

Examples 19-23 (formulations without additives)

| Ingredients | 19 Wt. % Active | 20 Wt. % Active | 21 Wt. % Active | 22 Wt. % Active | 23 Wt. % Active |
|---|---|---|---|---|---|
| ALPHA-STEP ® PC-48 | 6.0 | 6.0 | 6.0 | 6.0 | 6.0 |
| LATHANOL ® LAL | 6.0 | 6.0 | 6.0 | 6.0 | 6.0 |
| ALPHA-STEP ® MC-48 | 3.0 | | | | |
| ALPHA-STEP ® DS-85 | | 3.0 | | | |
| ALPHA-STEP ® PS-70 | | | 3.0 | | |
| ALPHA-STEP ® PS-65 | | | | 3.0 | |
| AMPHOSOL ® HCG | | | | | 3.0 |
| WATER | 85.0 | 85.0 | 85.0 | 85.0 | 85.0 |

TABLE F

Examples 24-29 (formulations with additives)
Examples 24-29 are formulations of the presently described cleansing composition, with selected additives, indicated in weight percent active.

| Ingredient | 24 Wt. % Active | 25 Wt. % Active | 26 Wt. % Active | 27 Wt. % Active | 28 Wt. % Active | 29 Wt. % Active |
|---|---|---|---|---|---|---|
| ALPHA-STEP ® PC-48 | 6.0 | 6.0 | 6.0 | 6.0 | 6.0 | |
| LATHANOL ® LAL | 6.0 | 6.0 | 6.0 | 6.0 | 6.0 | |
| ALPHA-STEP ® BSS-45 | | | | | | 12 |
| AMPHOSOL ® HCG | 3.0 | 3.0 | 3.0 | | | 3.0 |
| UCARE ® JR-400 | 0.4 | | | | 0.4 | 0.4 |
| $C_{20-24}$ AOS | 3.0 | | 3.0 | 3.0 | 3.0 | 3.0 |

TABLE F-continued

Examples 24-29 (formulations with additives)
Examples 24-29 are formulations of the presently described cleansing composition, with selected additives, indicated in weight percent active.

| Ingredient | Example 24 Wt. % Active | 25 Wt. % Active | 26 Wt. % Active | 27 Wt. % Active | 28 Wt. % Active | 29 Wt. % Active |
|---|---|---|---|---|---|---|
| PATIONIC ® SBL (Sodium Behenyl Lactylate) | | 3.0 | 3.0 | | | |
| ZELEC ® UN | | | | 3.0 | 3.0 | |
| Soybean Oil | 7.0 | 7.0 | 7.0 | 7.0 | 7.0 | 7.0 |
| Myristic Acid | 2.0 | | | 2.0 | 2.0 | |
| Petrolatum | | | 3.0 | | | |
| Glydant | 0.125 | 0.125 | 0.125 | 0.125 | 0.125 | 0.125 |
| Water | q.s. to 100 | q.s. to 100 | q.s. to 100 | q.s. to 100 | q.s. to 100 | q.s. to 100 |

TABLE G

Example 30 (Control Formulation)
Example 30 is a control formulation, for testing comparison, indicated in weight percent active.

| Ingredient | Example 30 Wt. % Active |
|---|---|
| STEOL ® CS-230 | 12.0 |
| AMPHOSOL ® HCG | 3.0 |
| WATER | 85.0 |

TABLE H

Examples 31-33 (Samples With Only SME/SFA)
Examples 31-33 contain only SME/SFA, without any ASA/EASA.

| Ingredient | Example 31 Wt. % Active | 32 Wt. % Active | 33 Wt. % Active |
|---|---|---|---|
| ALPHA-STEP ® PC-48 | 12.0 | | |
| ALPHA-STEP ® BSS-45 | | 12.0 | |
| ALPHA-STEP ® PS-65 | | | 12.0 |
| AMPHOSOL ® HCG | 3.0 | 3.0 | 3.0 |
| WATER | 85.0 | 85.0 | 85.0 |

All examples of the presently described technology were prepared in de-ionized water. The final pH of each composition was adjusted to between 5-6 with either sodium hydroxide (50%) or citric acid (50%). Foaming and skin feel evaluation for all examples was carried out using an in-vivo human expert panel test. Formulations according to the present technology were compared to a 15% active formulation containing sodium laureth sulfate and cocamidopropyl betaine control formulation (example 30) at a 4:1 active ratio (STEOL® CS-230/AMPHOSOL® HCG), or to a commercial product (Caress® body wash and Dove® Moisturizing Body Wash by Unilever, Softsoap® hand-soap by Colgate-Palmolive, or TreSemme® shampoo by Alberto-Culver).

Three panelists with different skin types (dry, normal, and moist) were chosen for each test. The skin type of the panelist was determined using a NOVA meter. A NOVA reading less than 100 represents dry skin, 110-130, normal skin and 130 or above, moist skin. The panelists were asked to assess the performance of the experimental product and the control or commercial product in a blind test using a 1 to 5 rating scale, with 1 being the worst and 5 being the best. Panelists were not told which samples were the experimental formulations, and which samples were the control or commercial product.

Panelists were asked to assess the following characteristics during and after the washing procedure: foam volume, skin softness, skin dryness, and tackiness during drying. To identify tackiness during drying, the panelists were instructed that some products may impart a sticky/tacky feel on the skin during the transition from a wet to a dry stage. Tackiness can be assessed by touching the fingers of the same hand together or by force required to separate fingers. To identify skin tightness when dry, the panelists were instructed that some products may leave the skin feeling tight or stretched after the skin is completely dry. The panelists were instructed that this property should not be evaluated until the panelist is sure that the hands are completely dry. Similarly, skin dryness was evaluated once the hands were completely dry.

To identify skin softness, the panelists were instructed to characterize how soft and smooth the skin feels to the touch. A product can often leave the skin feeling dry, but smooth. The positive extreme would be a smooth velvety feel (ranking of 5 on a 1-5 scale), and the opposite would be a rough feeling skin with some grittiness (ranking of 1 on a 1-5 scale). All samples were coded in order to get a fair comparison between the experimental and control products.

Human Panel Test Method
1. Panelists were asked to pre-wash their hands with 15% active sodium lauryl sulfate solution to remove residue from the skin and establish the baseline before evaluating of experimental body washes.
2. Hand washing tests were conducted using luke-warm (95° F. and 105° F.) running tap water.
3. Using a syringe, 1 ml of the 15% active body wash test product was dispensed to the panelist's wet palm.
4. The panelists were asked to wash their hands by gently rubbing them together for 30 seconds followed by rinsing under running tap water for 15 seconds.
5. The panelists were asked to rank the product for wet properties using a 1-5 scale.
6. The hands were dried using paper towel, and then evaluated for wet to dry stage transition properties.
7. Skin feel evaluation was done at ambient temperature (~25° C.).

The average response for the three panelists, for each experimental formulation, subtracted from the average response for the control formulation, is indicated below in Table I. A positive score indicates that the experimental formulation outperformed the control.

TABLE I

Performance Comparison of Experimental Compositions to Control Formulation (Example 30) (Control Score Subtracted from Average Values for Experimental Compositions)

| | Property | | |
|---|---|---|---|
| Example | Moisturization | Softness | Foam |
| Control Formulation (30) | 0 | 0 | 0 |
| Example 1 | 1.0 | 1.0 | 0 |
| Example 2 | 0.0 | 0.3 | 0.7 |
| Example 3 | 0.3 | 1.0 | −0.3 |
| Example 4 | 1.0 | 0.7 | 0.0 |
| Example 5 | 0.3 | 1.0 | 0.0 |
| Example 6 | 0.3 | 0.7 | 0.0 |
| Example 7 | 0.0 | 0.3 | 0.0 |
| Example 9 | 0.7 | 1.0 | 0.7 |
| Example 10 | 0.7 | 1.0 | −0.7 |
| Example 11 | 0.3 | 0.7 | 0.0 |
| Example 12 | 0.3 | 0.7 | 1.0 |
| Example 13 | 0.3 | 1.0 | −0.7 |
| Example 14 | 0.7 | 1.0 | 0.0 |
| Example 15 | 0.3 | 1.3 | 0.0 |
| Example 16 | 0.0 | 0.7 | 0.7 |
| Example 17 | 0.7 | 0.7 | 0.7 |
| Example 18 | 0.3 | 0.3 | 0.7 |

TABLE J

Comparison of Experimental Formulations to Caress ® Body Wash

| | Moisturization | Softness | Foaming |
|---|---|---|---|
| Caress ® Body Wash | 0 | 0 | 0 |
| Example 7 | 0.7 | 1.0 | 1.3 |
| Example 12 | 0.3 | 1.0 | 2.0 |
| Example 16 | 0.3 | 0.7 | 0.7 |
| Example 33 | 0.0 | 0.7 | −0.7 |

TABLE K

Comparison to Softsoap ® Hand Soap
Two samples with a mixture of Alpha-Step and Lathanol LAL were compared to Softsoap ® Hand Soap. Additionally, two samples with SME/SFA alone (Examples 31 & 32) were compared.

| | Property | | |
|---|---|---|---|
| Example | Softness | Moisturization | Foaming |
| Softsoap ® Hand Soap | 0 | 0 | 0 |
| Example 9 | 0.5 | 0.3 | 1.0 |
| Example 17 | 0.8 | 0.8 | 1.0 |
| Example 31 | 0.7 | 0.7 | 1.3 |
| Example 32 | 0.3 | 0.3 | 1.0 |

TABLE L

Comparison of Experimental Formulations to Dove ® Moisturizing Body Wash

| | Softness | Moisturization | Foaming |
|---|---|---|---|
| Dove ® Moisturizing Body Wash | 0 | 0 | 0 |
| Example 24 | 0.3 | 0.8 | 1.3 |
| Example 25 | 0.3 | 0.8 | 2.0 |
| Example 26 | −0.3 | 0.3 | 1.8 |
| Example 27 | 0.3 | 0.5 | 1.5 |
| Example 28 | 0.3 | 0.5 | 1.5 |
| Example 29 | 0.5 | 0.5 | 2.5 |

As can be seen in Tables I through L, each experimental formulation of the presently described technology performed equal to or better than the control formulation, Caress® Body Wash, or Soft-Soap® Hand Soap in softness, moisturizing, and foam volume. Additionally, each experimental formulation of the presently described technology, with added emollient, performed equal to or better than Doves Moisturizing Body Wash.

TABLE M

Examples 34-37 (formulations with high emollient concentration)
Examples 34-37 are formulations of the presently described cleansing composition, with high levels of emollient, indicated in weight percent active.

| | Example | | | |
|---|---|---|---|---|
| Ingredients | 34 Wt. % Active | 35 Wt. % Active | 36 Wt. % Active | 37 Wt. % Active |
| STEOL CS-230 ® | | | 6.0 | 6.0 |
| ALPHA-STEP ® PC-48 | 6.0 | 6.0 | 3.0 | 3.0 |
| LATHANOL ® LAL | 6.0 | 6.0 | 3.0 | 3.0 |
| AMPHOSOL ® HCG | 3.0 | 3.0 | 3.0 | 3.0 |
| Petrolatum | 25.0 | | 25.0 | |
| Soybean Oil | | 25.0 | | 25.0 |
| Emulsifier | 3.0 | 3.0 | 3.0 | 3.0 |
| D.I. WATER | q.s. to 100 | q.s. to 100 | q.s. to 100 | q.s. to 100 |
| Preservative | q.s. | q.s. | q.s. | q.s. |

TABLE N

Examples 38-39 (control formulations)
Examples 38 and 39 are control formulations, for testing comparison, indicated by weight percent active.

| | Example | |
|---|---|---|
| Ingredients | 38 Wt. % Active | 39 Wt. % Active |
| STEOL CS-230 ® | 12.0 | 12.0 |
| AMPHOSOL ® HCG | 3.0 | 3.0 |
| Petrolatum | 25.0 | |
| Soybean Oil | | 25.0 |
| Emulsifier | 3.0 | 3.0 |
| D.I. WATER | q.s. to 100 | q.s. to 100 |
| Preservative | q.s. | q.s. |

Foaming properties of the Examples 34-37 and 38-39 were measured using the following procedure:

Test Method

1. Hand wash tests were conducted using luke-warm (about 95° F. to about 105° F.) running tap water.
2. Using a syringe, 1 ml of the cleansing composition was dispensed to the panelist's wet palm.
3. Panelists washed their hands by working the product into foam for 30 seconds followed by rinsing under running tap water for 15 seconds.
4. The washing procedure was repeated one more time.
5. The foam from the second washing procedure was collected by having the panelists use their hands to scrape the foam from their hands and transfer the foam into a graduated beaker for foam volume measurement.

Foaming properties of the formulations of the present technology in Examples 34-37 were evaluated and compared to the control formulations of Examples 38-39. Each formulation contained a high level of emollient (e.g., 25% active). The results of the foaming test are graphically illustrated in FIG. 1.

As can be seen from the graph in FIG. 1, the experimental formulations of Examples 34 and 35, in accordance with the presently described technology, achieved a foam volume of 150 ml with 25% by weight of soybean oil included in the formulation and a foam volume of 125 ml with 25% by weight of petrolatum included in the formulation. In comparison, the control formulations (Examples 38 and 39), had a foam volume of only 75 ml with the same amount of soybean oil included in the control formulation, and a foam volume of only 55 ml with the same amount of petrolatum included in the control formulation. Thus, the formulation in accordance with the present technology that comprised 25% by weight soybean oil (Example 35), had a foam volume that was double that of the comparable control formulation (Example 39), and the formulation in accordance with the present technology that comprised 25% by weight petrolatum (Example 34) had a foam volume that was more than double that of the comparable control formulation (Example 38). This represents a surprising and significant improvement in foaming performance compared to the control formulation.

Further, Examples 36 and 37 demonstrate that improved foaming performance compared to the control formulation can still be achieved when the primary surfactant of the formulation of the presently described technology only partially replaces the STEOL CS-230 of the control formulation. In Examples 36 and 37, the formulations contained 3% active ALPHA-STEP® PC-48 and 3% LATHANOL® LAL, a primary surfactant system in accordance with the presently described technology, and 6% active STEOL CS-230, rather than the 6% active ALPHA-STEP® PC-48 and 6% LATHANOL® LAL, used in Examples 34 and 35, or the 12% active STEOL CS-230 used in control Examples 38 and 39. As can be seen from the graph in FIG. 1, improved foaming performance, as compared to the control formulations can still be achieved even though the primary surfactant system of the presently described technology only partially replaces the conventional primary surfactant used in the control examples.

In addition to body washes and hand washes, compositions according to the presently described technology may also be configured as shampoos. A simple formulation according to the present technology, without thickeners or additives which may be added as desired for a shampoo, was compared to a leading commercially available shampoo, TreSemme® available from Alberto-Culver in a salon test. The formulations of experimental formulation Examples 40 and 41 are indicated in Table O. The experimental formulations were tested by 18 individuals, and compared on a number of properties, as indicated in Table P.

TABLE O

Experimental Formulations for Shampoo Testing

| Ingredient | Example 40 Wt. % Active | Example 41 Wt. % Active |
|---|---|---|
| Alpha-Step ® PC-48 | 6.0 | |
| Alpha-Step ® BSS-45 | | 6.0 |
| LATHANOL ® LAL | 6.0 | 6.0 |
| AMPHOSOL ® HCG | 3.0 | 3.0 |
| Water | 85.0 | 85.0 |

TABLE P

Comparison of Example 40 and Example 41 to TreSemme ® by Alberto-Culver

| Evaluation Parameters | Example 40 | | | | Example 41 | | | |
|---|---|---|---|---|---|---|---|---|
| | Obvious Difference | Noticeable Difference | Slightly Better | Equal | Obvious Difference | Noticeable Difference | Slightly Better | Equal |
| Flash Foam | | | | 10* | | | | 8 |
| Foam Volume | 4 | | 5 | 1 | 4 | | 4 | |
| Foam Stability | | | | 10 | | | | 8 |
| Foam Density | | | | 10 | | | | 8 |
| Rinsability | | | | 10 | | | | 8 |
| Detangling | | 1 | 1 | 8 | | | 3 | 5 |
| Wet Compatibility | | | 3 | 7 | | | 6 | 2 |
| Dry Compatibility | | | 2 | 8 | | | 2 | 6 |
| Absence of Static | | | | 10 | | | | 8 |
| Body | | | | 10 | | | | 8 |
| Shine | | | | 10 | | | | 8 |

*Indicating, for example, 10 participants who judged flash foam to be equal to TreSemme ®.

As can be seen in Table P, the experimental formulations performed better or equal to TreSemme® in flash foam, foam stability, foam density, rinsability, detangling, combabilty, absence of static, body, and shine.

Other simple shampoo formulations according to the present technology, without thickeners or additives which may be added as desired for a shampoo, are compared for color washing fastness to a shampoo formulation based upon 15% active STEOL CS-230/Amphosol HCG in a 4:1 active ratio. The experimental formulations and the control formulation are indicated in Table Q.

TABLE Q

Experimental Formulations and Control Formulation for Color Washing Fastness Testing

| | Example | | | |
|---|---|---|---|---|
| Ingredient | Example 42 Wt. % Active | Example 43 (control) Wt. % Active | Example 44 Wt. % Active | Example 45 Wt. % Active |
| ALPHA-STEP ® PC-48 | 6.0 | | 2.5 | 10.0 |
| LATHANOL ® LAL | 6.0 | | 2.5 | 10.0 |
| STEOL ® CS-230 | | 12.0 | | |
| AMPHOSOL ® HCG | 3.0 | 3.0 | 2.0 | 2.0 |
| D.I. Water | 85.0 | 85.0 | 93.0 | 78.0 |

Examples 42 and 43 were tested and compared for color washing fastness, which evaluates the ability of colored hair to maintain its color through shampoo washings. The following test method was used to evaluate the color washing fastness of Example 42 and control Example 43.

Color Washing Fastness Test Method

1. Initial color measurement was taken on 2 g European brown hair colored swatch (blond hair colored with dark brown permanent (oxidation) color—Wella Dark Brown Color #311) using a Minolta Colorimeter.
2. The hair swatch was wet with lukewarm (T=about 96° to about 98° F.) tap water.
3. 1 g of test shampoo composition was applied to 2 g hair swatch. The shampoo was worked into a foam using fingers for 30 seconds
4. The hair swatch was rinsed for 30 seconds under running tap water.
5. The procedure was repeated 3, 5 and 10 times. The hair swatch was air-dried and the total color $\Delta E^*_{ab}$ were measured before washing and after 3 washings, 5 washings and 10 washings using the Minolta Colorimeter.

$$\Delta E^*_{ab} = \sqrt{(\Delta L^*)^2 + (\Delta a^*)^2 + (\Delta b^*)^2}$$

where

L*=lightness a*=+red/−green b*=+red/−blue

6. The color difference $\Delta E^*$ before and after washing was calculated using the following equation:

$$\Delta E^* = \Delta E^*_{ab\ (after\ washing)} - \Delta E^*_{ab\ (initial)}$$

The results from the color washing fastness tests are shown in Table R.

TABLE R

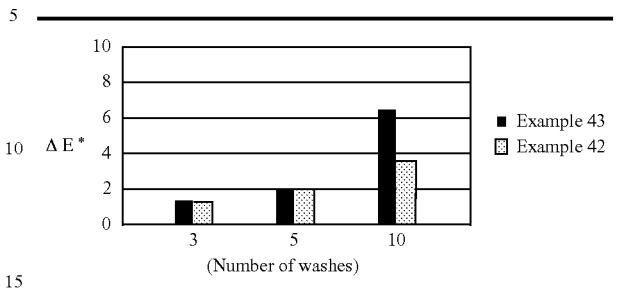

(Number of washes)

As can be seen from Table R, the shampoo formulation of Example 42, in accordance with the presently described technology, showed significant observable improvement in $\Delta E^*$ color washing fastness compared to the Example 43 control after 10 washing cycles. The difference between formulation 42 and formulation 43 in $\Delta E^*$ after 10 washing cycles was 3.38.

Conditioning shampoo formulations according to the presently described technology, which contain silicone oil as an added component, were prepared in accordance with the procedure set forth below. The experimental formulations for the conditioning shampoo are indicated in Examples 46 and 47 in Table S.

TABLE S

Conditioning Shampoo Formulations

| | Example | |
|---|---|---|
| Ingredient | Example 46 Wt. % Active | Example 47 Wt. % Active |
| D.I. Water | q.s. to 100 | q.s. to 100 |
| ALPHA-STEP ® PC-48 | 6.0 | 3.0 |
| LATHANOL ® LAL | 6.0 | 3.0 |
| STEOL CS-230 | | 6.0 |
| AMPHOSOL ® HCG | 3.0 | 3.0 |
| Stepan EGMS (ethylene glycol monostrearate) | 2.0 | 2.0 |
| Silicone Fluid DC 200 (12,500 cps, dimethicone) | 2.0 | 2.0 |
| Glydant | 0.125 | 0.125 |

Mixing Procedure

1. Mix water and surfactants, and heat the mixture to about 65° C.
2. Add EGMS, mix until dispersed.
3. Add Silicone Fluid DC 200, mix well for 30 minutes. Start cooling.
4. Add Glydant at about 25° C.
5. Check pH. Adjust with NaOH or citric acid, if necessary, to obtain a pH of about 5 to about 6.
6. Adjust viscosity with NaCl, if necessary.

The formulations of Examples 46 and 47 show good foaming and emulsification properties, even though the formulations contain 2.0 weight percent active silicone oil (Silicone Fluid DC 200).

TABLE T

Examples 48-52 (formulations without additives)

| Component | Example 48 Wt % Active | Example 49 Wt % Active | Example 50 Wt % Active | Example 51 Wt % Active | Example 52 Wt % Active |
|---|---|---|---|---|---|
| ALPHA-STEP ® PC-48 | 8.0 | 10.0 | 11.0 | 4.8 | 6.0 |
| LATHANOL ® LAL | 4.0 | 2.0 | 1.0 | 7.2 | |
| Sodium ethoxylated alkyl sulfoacetate | | | | | 6.0 |
| AMPHOSOL ® HCG | 3.0 | 3.0 | 3.0 | 3.0 | 3.0 |
| Water | 85.0 | 85.0 | 85.0 | 85.0 | 85.0 |

Examples 48-52 are formulations of the presently described cleansing composition, without any additives or thickeners, indicated in weight percent active. These formulations illustrate that different ratios of primary surfactant components may be used in the cleansing composition of the presently described technology. Also, Example 52 illustrates that an ethoxylated alkyl sulfoacetate (EASA) may be used as a primary surfactant component in the cleansing composition of the presently described technology.

The invention has now been described in such full, clear, concise and exact terms as to enable any person skilled in the art to which it pertains, to practice the same. It is to be understood that the foregoing describes preferred embodiments and examples of the invention and that modifications may be made therein without departing from the spirit or scope of the invention as set forth in the claims.

The invention claimed is:

1. A liquid cleansing composition comprising:
   (a) between about 0.1% to about 70% by weight of a primary surfactant mixture comprising:
      (i) an alpha sulfonated alkyl ester of a fatty acid;
      (ii) a sulfonated fatty acid, and (iii) an alkyl sulfoacetate, wherein the ratio of the alpha sulfonated alkyl ester of a fatty acid and sulfonated fatty acid, in combination, to the alkyl sulfoacetate is between about 1:1.5 to about 10:1;
   (b) between about 0.1% to about 15% by weight of secondary surfactants;
   (c) optionally between about 0.1% to about 50% by weight of additives, and
   (d) balance with water up to 100%.

2. The composition of claim 1, wherein the alpha sulfonated alkyl ester has the formula:

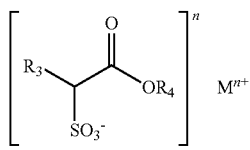

wherein $R_3$ is a fully saturated or unsaturated $C_6$-$C_{22}$ hydrocarbyl group, an alkyl group, or a combination thereof, $R_4$ is a straight or branched chain $C_1$-$C_6$ hydrocarbyl group, an alkyl group, or a combination thereof, n is an integer equal to 1 or 2, and M is a member of the group consisting of hydrogen, sodium, potassium, calcium, magnesium, ammonium, monoethanolammonium, diethanolammonium, triethanolammonium, and mixtures thereof.

3. The composition of claim 1, wherein the sulfonated fatty acid has the formula:

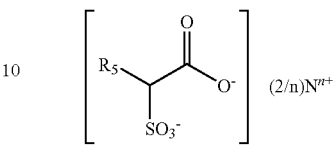

wherein $R_5$ is a fully saturated or unsaturated $C_6$-$C_{22}$ hydrocarbyl group, an alkyl group, or a combination thereof, n is an integer equal to 1 or 2, and N is a member of the group consisting of hydrogen, sodium, potassium, calcium, magnesium, ammonium, monoethanolammonium, diethanolammonium, triethanolammonium, and mixtures thereof.

4. The composition of claim 1, wherein the alkyl sulfoacetate or ethoxylated alkyl sulfoacetate has the chemical structure:

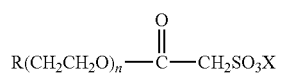

wherein R is a fully saturated or unsaturated $C_7$-$C_{21}$ hydrocarbyl group, n is an integer between 0 and 6, and X is hydrogen, an alkaline metal, ammonium, organic amine, or alkaline earth metal.

5. The composition of claim 1, wherein the ratio of the alpha sulfonated alkyl ester and the sulfonated fatty acid in combination to the alkyl sulfoacetate is between about 1:1.5 to about 4:1.

6. The composition of claim 1, wherein the primary surfactant mixture further comprises an ethoxylated alkyl sulfoacetate.

7. The composition of claim 1, wherein the primary surfactant mixture comprises between about 1% to about 35% by weight of the total cleansing composition.

8. The composition of claim 7, wherein the primary surfactant mixture comprises between about 3% to about 20% by weight of the total cleansing composition.

9. The composition of claim 1, further comprising between about 0.01% to about 50% by weight of one or more additives selected from the group consisting of emollients, emulsifiers, rheological modifiers, humectants, salts, skin conditioning agents, fragrances, colors, herbal extracts, builders, enzymes, pH adjusters, antibacterial agents, vitamins, antioxidants, pearlescent agents, opacifiers, and preservatives.

10. The composition of claim 9, comprising between about 1% to about 10% by weight of the additive.

11. The composition of claim 9, comprising one or more emollients selected from the group consisting of vegetable oils, mineral oils, silicone oils, petrolatums, polyglycerol esters, methyl esters, and other emollient esters.

12. The composition of claim 9, comprising one or more rheological modifiers selected from the group consisting of polyacrylic acid, polyacrylate, polyvinyl alcohol, polyethylene glycol, polyethylene glycol ester, cellulose derivatives, starch derivatives, sodium chloride, potassium chloride, magnesium chloride, sodium sulfate, potassium sulfate, magnesium sulfate, and calcium chloride.

13. The composition of claim 1, wherein the secondary surfactant is an anionic surfactant selected from the group consisting of a salt of alkyl benzene sulfonates, alpha olefin sulfonates, paraffin sulfonates, alkyl sulfates, alkyl alkoxy sulfates, alkyl alkoxy carboxylates, alkyl phosphates, alkyl alkoxy phosphates, alkyl sulfonates, alkyl alkoxylated sulfates, alkyl isethionates, acyl lactylates, salts thereto, and combinations thereof.

14. The composition of claim 1, wherein the secondary surfactant is a non-ionic surfactant selected from the group consisting of fatty acid amides, ethoxylated fatty acid amides, alkyl alcohols, alkyl alcohol ethoxylates, alkyl phenol ethoxylates, propylene glycol esters, poly glycerol esters, ethylene glycol esters, ethoxylated glycol esters, polypropylene glycol esters, alkylpolyglycosides, alkyl glucamides and combinations thereof.

15. The composition of claim 1, wherein the secondary surfactant is selected from the group consisting of betaines, amine oxides, hydroxysultaines, sulfosuccinates, amphoacetates, sarcosinates, and acyl lactylates.

16. The composition of claim 1, wherein the secondary surfactant is a cationic agent or a cationic polymer selected from the group consisting of alkyl dimethylammonium halogenide, quaternized cellulose, quaternized guar gum, esterquat, amidoquat, and stearylammidopropyl dimethyl amine quat.

17. The composition of claim 1, wherein the composition is incorporated into a powder or a gel.

18. A process for producing a primary surfactant composition comprising:
(a) combining in a reaction vessel
  (i) alkyl alcohol mono-chloroacetate or ethoxylated alkyl alcohol mono-chloroacetate and
  (ii) sulfonated alkyl ester and sulfonated fatty acid
(b) sulfitating with sodium sulfite and sodium metabisulfite of (i) in the presence of (ii) to produce alkyl sulfoacetate or ethoxylated alkyl sulfoacetate, and sulfonated alkyl ester and sulfonated fatty acid in a ratio of the sulfonated alkyl ester and sulfonated fatty acid combination to alkyl sulfoacetate or ethoxylated alkyl sulfoacetate of between about 1:1.5 to about 10:1; and
(c) neutralizing the mixture generated in step (b) with alkaline solution to produce a primary surfactant mixture comprising between about 0.5% to about 70% by weight total surfactant.

19. A composition suitable for use as a skin cleanser or shampoo comprising:
(a) between about 1% to about 30% by weight of a primary surfactant mixture comprising: (i) an alpha sulfonated alkyl ester of a fatty acid;
(ii) a sulfonated fatty acid; and (iii) an ethoxylated alkyl sulfoacetate, wherein the ratio of wherein the ratio of the alpha sulfonated alkyl ester of a fatty acid and sulfonated fatty acid, in combination, to the ethoxylated alkyl sulfoacetate is between about 1:3 to about 10:1;
(b) between about 0.1% to about 15% by weight of secondary surfactants;
(c) between about 0.1% to about 50% of optional additives; and
(d) water.

20. The composition of claim 19, wherein the secondary surfactant is selected from the group consisting of sulfonated alkyl benzenes, sulfonated alpha olefins, sulfonated paraffins, alkyl sulfates, alkyl alkoxy sulfates, alkyl alkoxy carboxylates, alkyl phosphates, alkyl alkoxy phosphates, sulfonated alkyls, alkyl alkoxylated sulfates, acyl lactylates, fatty acid amides, ethoxylated fatty acid amides, alkyl alcohols, alkyl alcohol ethoxylates, alkyl phenol ethoxylates, propylene glycol esters, poly glycerol esters, betaines, sultaines, alkyl isethionates, amine oxides, glucamides, alkyl polyglycosides, sulfosuccinates, amphoacetates, sarcosinates and mixtures thereof.

21. The composition of claim 19, further comprising between about 0.01% to about 20% by weight of an additive selected from the group consisting of emollients, emulsifiers, rheological modifiers, humectants, salts, skin conditioning agents, fragrances, colors, herbal extracts, vitamins, builders, enzymes, pH adjusters, antibacterial agents, preservatives, opacifiers, pearlescent agents, and mixtures thereof.

22. A colorfast shampoo composition comprising:
(a) from about 5 to about 25 weight percent active of a primary surfactant mixture comprising:
  (i) an alpha sulfonated alkyl ester of a fatty acid;
  (ii) a sulfonated fatty acid; and
  (iii) an alkyl sulfoacetate, an ethoxylated alkyl sulfoacetate, or a mixture thereof, in a ratio of (i) and (ii) in combination, to (iii) of about 10:1 to about 1:10;
(b) from about 0.5 to about 10 weight percent active of a secondary surfactant;
(c) from about 0.1 to about 10 weight percent of additives, and
(d) water.

23. The composition of claim 19, wherein the primary surfactant mixture further comprises an alkyl sulfoacetate.

* * * * *